(12) United States Patent
Ho et al.

(10) Patent No.: US 8,932,498 B2
(45) Date of Patent: Jan. 13, 2015

(54) DEVICE FOR PREPARATION OF LIPOSOMES AND METHOD THEREOF

(75) Inventors: JA-An Ho, Hsinchu (TW); Yeh-Chun Lin, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 646 days.

(21) Appl. No.: 12/870,693

(22) Filed: Aug. 27, 2010

(65) Prior Publication Data

US 2011/0163468 A1   Jul. 7, 2011

(30) Foreign Application Priority Data

Jan. 7, 2010   (TW) ................................. 99100286 A

(51) Int. Cl.
| | |
|---|---|
| *A61K 9/127* | (2006.01) |
| *B01J 8/00* | (2006.01) |
| *B01J 13/04* | (2006.01) |
| *B01J 13/12* | (2006.01) |

(52) U.S. Cl.
CPC ............... *A61K 9/127* (2013.01); *A61K 9/1277* (2013.01); *B01J 13/04* (2013.01); *B01J 13/125* (2013.01)
USPC ........................................... 264/4.1; 422/187

(58) Field of Classification Search
CPC .................................... A61K 9/127; B01J 8/00
See application file for complete search history.

(56) References Cited

U.S. PATENT DOCUMENTS

| | | | | |
|---|---|---|---|---|
| 5,626,751 | A | * | 5/1997 | Kikuchi et al. .......... 210/321.75 |
| 6,596,305 | B1 | * | 7/2003 | Edgerly-Plug ................ 424/450 |
| 7,419,796 | B2 | * | 9/2008 | Durst et al. .................. 435/7.92 |
| 2007/0197954 | A1 | * | 8/2007 | Keenan ........................... 604/20 |

OTHER PUBLICATIONS

Notice of Allowance of Taiwan counterpart Application No. TW 099100286 dated Aug. 22, 2013.
English Translation of Notice of Allowance of Taiwan counterpart Application No. TW 099100286 dated Aug. 22, 2013.

* cited by examiner

*Primary Examiner* — Randy Gulakowski
*Assistant Examiner* — Jeffrey Washville
(74) *Attorney, Agent, or Firm* — WPAT, P.C.; Anthony King

(57) ABSTRACT

Disclosed is a device for preparation of liposomes, comprises a reaction tank and an infusion unit. The reaction tank comprises a collector mounted in a predetermined position of the reaction tank; Two inlet ports are included: the first inlet port for infusing an aqueous solution; and the second inlet port for infusing an organic solution. The infusion unit can introduce a bioactive agent containing-aqueous solution into the reaction tank. The infusion unit comprises a filter connected to one end of the infusion unit and being adjacent to the collector. The method using the device comprises the steps of infusing an aqueous solution and an organic solution into the reaction tank of the device and thus forming an interface between the filter and the collector; infusing a bioactive agent containing-aqueous solution and being filtered by the filter, the bioactive agent is encapsulated to form a water-in-oil emulsion; the water-in-oil emulsion is passing through the aqueous solution and thus to form a water-in-oil-in-water double emulsion. Finally the removal of the organic phase of water-in-oil-in-water double emulsion enables the harvest a plurality of liposomes. It has advantages such that simple-used and automation production. Thus nano size or sub-micro size liposomes can be prepared with high encapsulation efficiency without sonicators or delicate microfluidic systems.

16 Claims, 9 Drawing Sheets

(A)

(B)

(C)

(A)

(B)

(C)

US 8,932,498 B2

DEVICE FOR PREPARATION OF LIPOSOMES AND METHOD THEREOF

FIELD OF THE INVENTION

The present invention relates to a device for production of liposomes, particularly relates to a device for production of liposomes based on the double emulsion method.

BACKGROUND OF THE INVENTION

Liposomes were first published by British hematologist Dr Alec D Bangham FRS in 1965, at the Babraham Institute, in Cambridge. Structurally, liposomes are holy spheres made of lipids, and have a diameter of approximately 0.025~3.5 μm, so that they can be immiscibly dispensed in aqueous phase. Lipid membranes of liposomes are present as bilayers and mainly composed of phospholipids. The phospholipids have a head group and a tail group. The head is attracted to water, and the tail, which is made of a long hydrocarbon chain, exactly like an erythrocyte membrane or cell membrane. Due to their bilayer structures, liposomes can be used to encapsulate both hydrophilic molecules (and ionic agent) and hydrophobic compounds, and thus can be used to be carriers for drug delivery. While being used for drug delivery, liposomes have various functions. For example, liposomes are suitable for encapsulating hydrophilic/ionic and hydrophobic drugs, and additionally have characteristics such as biocompatibility and biodegradability. They are capable of protecting drugs passing through metabolic systems to the target location of a human body. Liposomes also have the ability for lysis and release control, are suitable for being carriers for hydrophobic and hydrophilic agents. Thus, liposomes have great potential to apply in the fields of biomedicine, nanotechnology, bioanalysis or artificial cell membrane system.

The methods for preparation of liposomes include thin-film hydration method, ethanol injection method, reverse-phase evaporation method and double emulsion method, wherein the double emulsion method is highly related with the present invention.

With reference to FIG. 1(A)-1(E), which depict the conventional double emulsion method for preparation of liposomes. The process is simply described as follow. Firstly, high concentration lipids are dissolved in an organic solvent (FIG. 1A), and an aqueous solution is added and thus to be stably dispersed in the organic solvent to form an emulsion (FIG. 1B, 1C). Then the emulsion is added to water to form a water-in-oil-in-water double emulsion (W/O/W double emulsion) (FIG. 1D). Finally, the organic solvent is evaporated by a rotary evaporator or by placing for a while, so as to obtain bilayer liposomes (FIG. 1E). The liposome size is determined by the initial formed droplet size (emulsion). Although the double emulsion method may need a delicate microfluidic system, it has high encapsulation efficiency.

However, the traditional method for liposome production has many drawbacks. For example, encapsulation efficiency is too low. Additionally, the process for producing liposomes usually needs sonicators or microfluidic systems. Unfortunately, sonicators may lower the encapsulation efficiency, and microfluidic systems are merely able to produce micro-size liposomes. And the traditional methods are incapable of realizing programmable mass production.

SUMMARY OF THE INVENTION

It is an objective of the present invention to provide a device for liposome preparation to improve the drawbacks of low encapsulation efficiency and being incapable of programmable mass production.

It is another objective of the present invention to provide a method for liposome preparation to improve the drawbacks of low encapsulation efficiency and being incapable of programmable mass production.

In one embodiment of the present invention, the device comprises a reaction tank and an infusion unit. The reaction tank comprises: a collector mounted in a pre-determined position of the reaction tank; the first inlet port for infusing an aqueous solution; and the second inlet port for infusing an organic solution. The infusion unit can introduce a bioactive agent containing-aqueous solution into the reaction tank. The infusion unit comprises a filter connected to one end of the infusion unit and being adjacent to the collector, and another end of the infusion unit is adapted to introduce the bioactive agent containing-aqueous solution.

In another embodiment of the present invention, the method for preparation of liposomes comprises the steps of: providing an aqueous solution, an organic solution, and a bioactive agent containing-aqueous solution; infusing the aqueous solution and organic solution into the reaction tank of the device and thus forming an interface between the filter and the collector; introducing the bioactive agent containing-aqueous solution and being filtered by the filter, the bioactive agent is encapsulated to form a water-in-oil emulsion; the water-in-oil emulsion is then passing through the aqueous solution and form a water-in-oil-in-water double emulsion. The removal of the organic phase of water-in-oil-in-water double emulsion so as to harvest a plurality of liposomes.

The device according to the present invention is designed by means of, including, using syringe filter, glass device and the double emulsion-based method. It has advantages such that simple-used and automation production. Without utilization of sonicators or microfluidic systems, nano-size or sub-micro size liposomes can be prepared with high encapsulation efficiency. Thus, it is suitable to be applied in the fields of biomedicine, nanotechnology, bioanalysis or artificial cell membrane system.

DETAILED DESCRIPTION

Definition

1. Liposome

Liposomes are holy spheres composed of lipid bilayers, which are structurally similar to cell membranes, may contain certain amounts of aqueous solution. Liposomes can be used for gene delivery and therapy, targeted drug delivery and control release, and immunoassay.

2. Double Emulsion Method

Figure 1A:
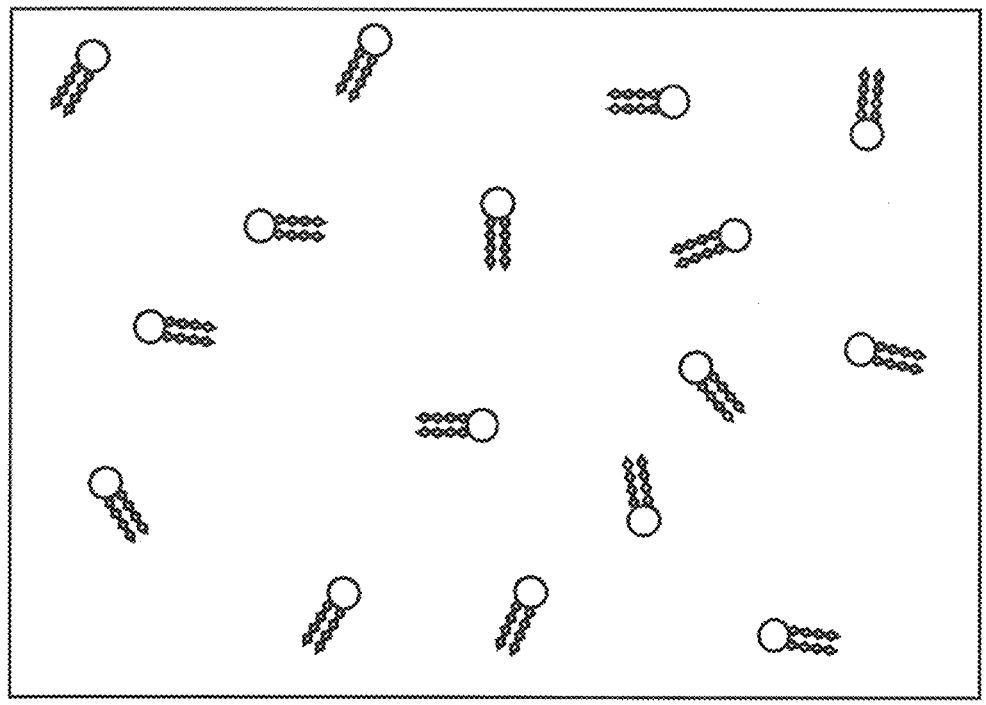
FIG. 1(A)-1(E) depict the conventional double emulsion method for preparation of liposomes.
Figure 1B:
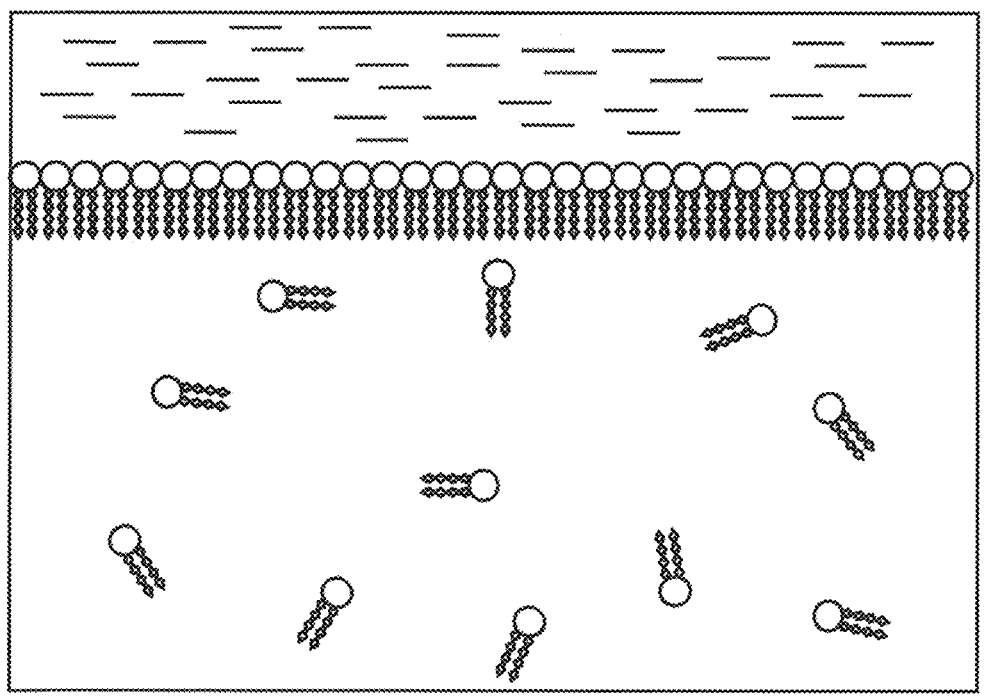
Figure 1C:
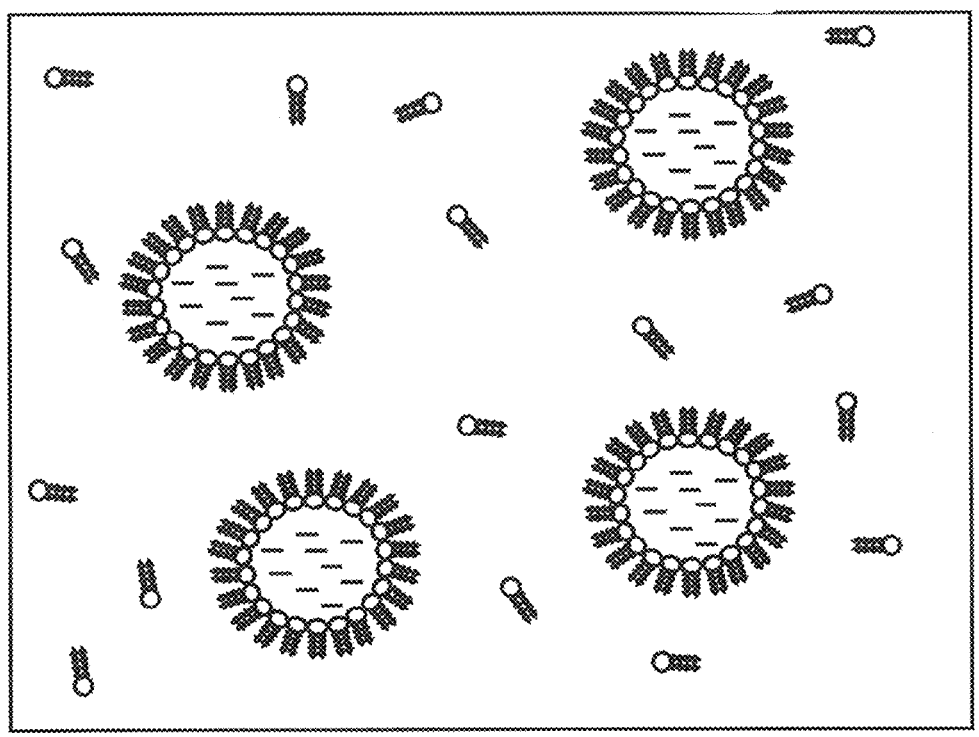
Figure 1D:
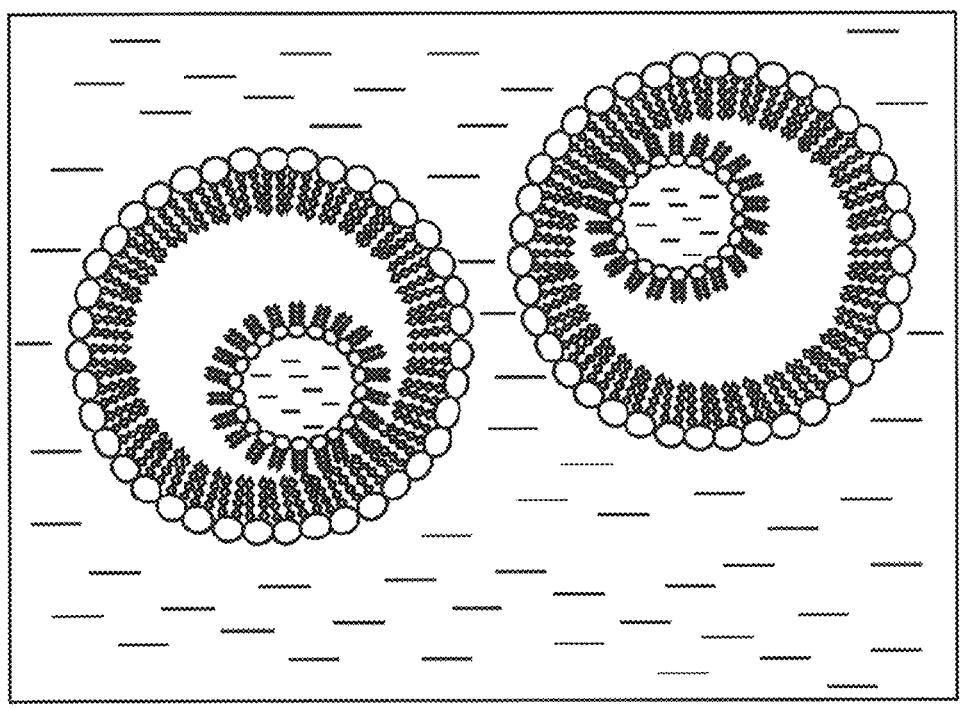
Figure 1E:
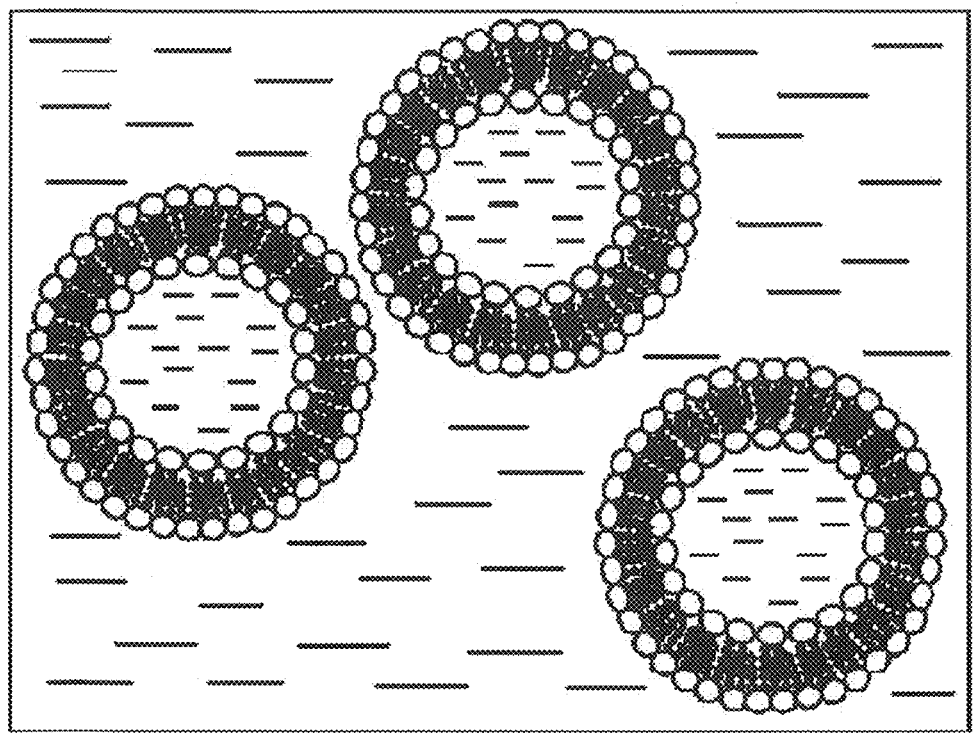

Double emulsion method is a technique that tiny bubbles are dispersed from two or more immiscible liquids. Firstly, high concentration lipids are dissolved in an organic solvent. A small amount of aqueous solution is added to the organic solvent and thus be stably dispersed therein to form an emulsion. Then the emulsion is added into water to form a water-in-oil-in-water double emulsion (W/O/W double emulsion). Finally, the organic solvent is evaporated by a rotary evaporator or by aging for a while to obtain bilayer liposemes (FIG. 1E).

3. Water-in-Oil-in-Water Double Emulsion (W/O/W Double Emulsion)

The W/O/W double emulsion is an emulsion, which can be considered as emulsions within emulsions. It composed of an internal aqueous part, and a hydrophobic component surrounded with an aqueous continuous phase.

4. Encapsulation Efficiency $$\frac{\text{amount of substance encapsulated by liposome}}{\text{total amount of used substance}} \times 100\%$$

Embodiment 1

Figure 2:
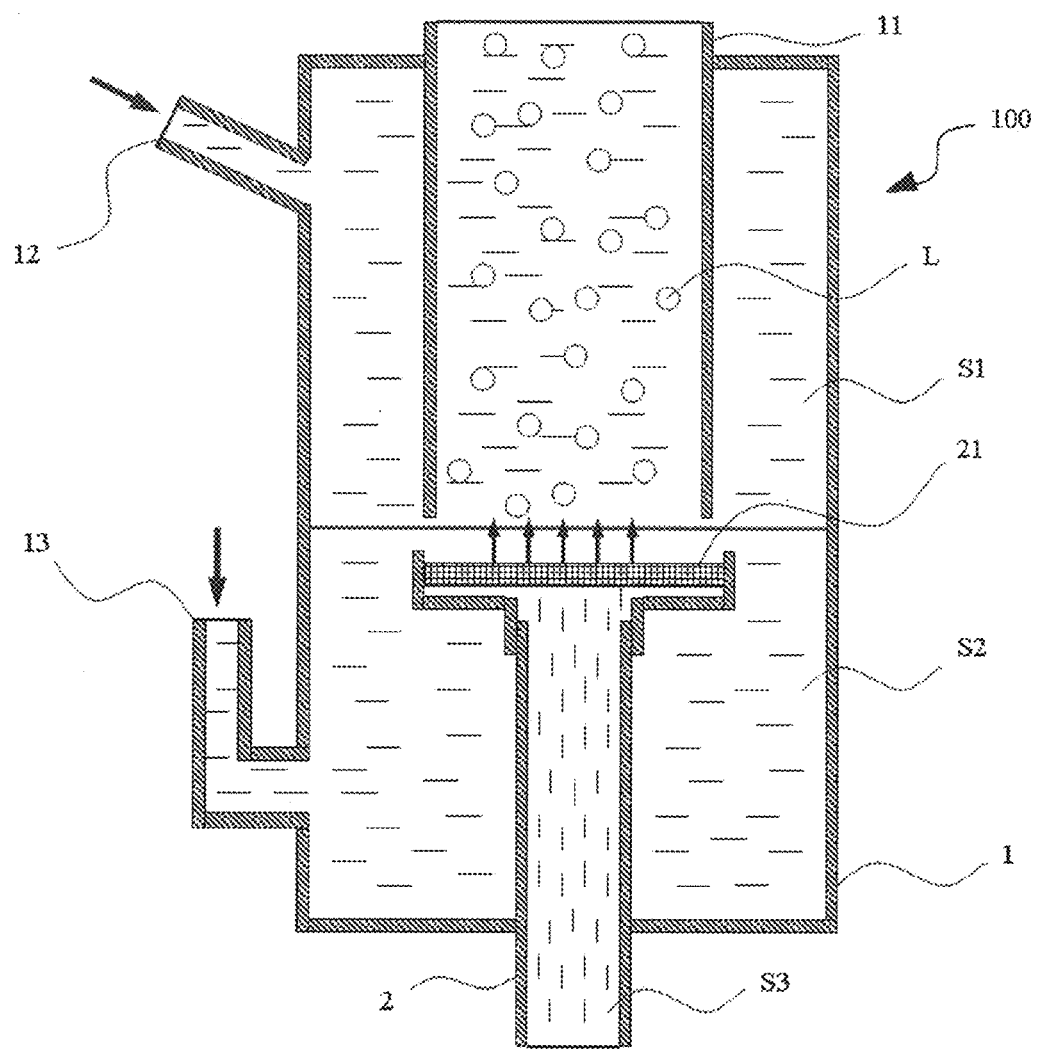
FIG. 2 depicts a sectional view of the device according to the first embodiment of the present invention.

With reference to FIG. 2, a sectional view of the device according to the first embodiment of the present invention. As shown in FIG. 2, the device 100 comprises a reaction tank 1 and an infusion unit 2. In this embodiment, reaction tank 1 is made of glass. However, reaction tank is, including but not limited to, glass device or any proper size container made of chemical/physical compatible material.

The reaction tank 1 comprises a collector 11, a first inlet port 12 and a second inlet port 13. The collector 11 is mounted at the bottom of the reaction tank 1 to collect the water-in-oil-in-water double emulsion L (W/O/W double emulsion). The first inlet port 12 and second inlet port 13 are adapted to infuse an aqueous solution S1 and an organic solution S2 into the collector 11 to form an interface. So that the organic solution S2 can be used to form liposomes, and the aqueous solution S1 can be provided to be an external part surrounding thereby. After that, liposomes can be harvested after removing the organic phase of the W/O/W double emulsion.

The infusion unit 2 comprises a filter 21. In this embodiment, filter 21 is, but not limited to a glass sieve, or other filter devices made of chemical/physical compatible material. For example, it can be a syringe filters. Nevertheless, the pore sizes of the filter devices relate to the formation of liposome size, so the ideal filter devices should be selected depend on actual requirements. The filter 21 is connected to one end of the infusion unit 2, and is adjacent to the collector 11. The other end of the infusion unit 2 is used to introduce a bioactive agent containing-aqueous solution S3 into the reaction tank 1. According to this embodiment, the bioactive agent is fluorescence dye. Furthermore, the bioactive agent can be a drug, protein, aptamer or contrast agent.

The manufacture process of liposomes using the device 100 of the present invention is described as follow. At first, the aqueous solution S1 and the organic solution S2 are infused into the reaction tank 1. Due to insolubility property between the organic and aqueous phase, two solutions contact each other and thus form an interface between the filter unit 21 and the collector 11. Once being infused into the reaction tank 1, the bioactive agent containing-aqueous solution S3 is filtered by the filter unit 21 firstly, and is then sequentially passed through the organic solution S2 and the aqueous solution S1. Finally, W/O/W double emulsion L is formed and enters into the collector 11 to be harvested.

Embodiment 2

Figure 3:
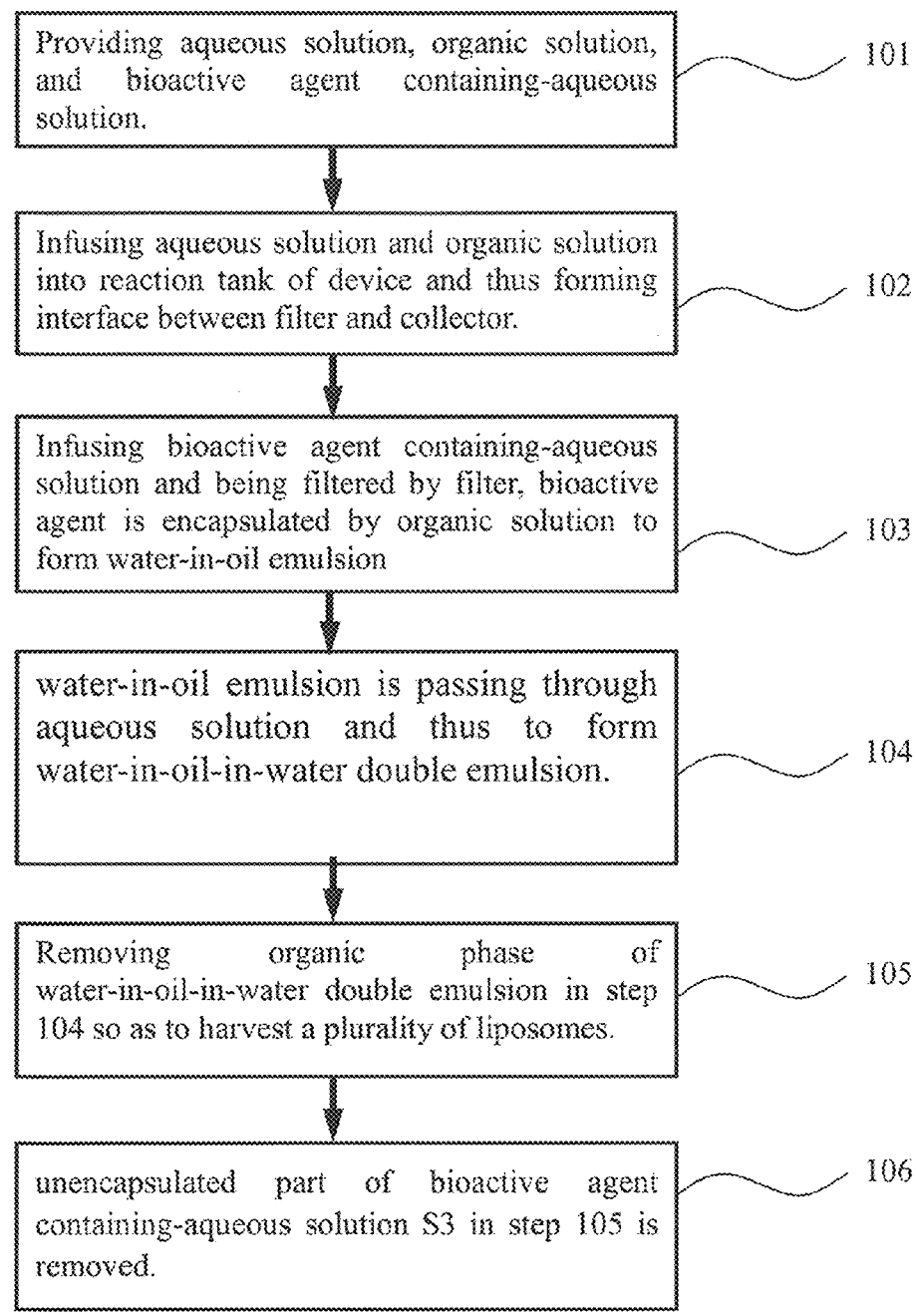
FIG. 3 depicts a flow chart of the device according to the second embodiment of the present invention.

With reference to FIG. 3, this is a flow chart of the device according to the second embodiment of the present invention. This embodiment is based on double emulsion method and uses the device 100 mentioned above (as shown in FIG. 2). Accordingly, the manufacture process of liposomes is simple and programmable, and particularly has high encapsulation efficiency.

Step 101: Providing an aqueous solution S1, an organic solution S2, and a bioactive agent containing-aqueous solution S3. The details of the process are described as follow:

(1) The organic solution S2 according to this embodiment is consisting of an organic solvent and at least one phospholipid. The organic solvent used here is chloroform, and the phospholipid includes dipalmitoylphosphatidylcholine (DPPC), dipalmitoylphosphatidylglycerol (DPPG) or other kinds of phospholipids are also workable. DPPG can be used to lower the aggregation level and increase the stability of liposomes), or other phospholipids. DPPC and DPPG (w/w ration=10:1) are added and dissolve in a proper volume of chloroform, so as to obtain the DPPC/DPPG solution. The solution is loaded in the syringe and to be the organic solution S2.

On the other hand, the organic solution S2 is added with 0.1 mM Nile red (a hydrophobic fluorescence dye, UV/Vis absorbance maximum: 543 nm, emission wavelength maximum: 610 nm). It is facilitated to observe the distribution of water and oil by fluorescence or laser scanning confocal microscope. The substance contained in the organic solution S2 is, including but not limited to fluorescence, drug or contrast agent.

(2) 5 ml of 5(6)-carboxyfluorescein (a hydrophilic fluorescence dye, UV/Vis absorbance maximum: 492 nm, emission wavelength maximum: 517 nm) solution with a determined concentration, is prepared by $ddH_2O$ and loaded in a plastic syringe (3 mL). It is to be the bioactive agent containing-aqueous solution S3 of the present embodiment.

(3) A plastic syringe (3 mL) is provided and loaded with $ddH_2O$ which is the aqueous solution S1 of the present embodiment.

(4) While the preparation is done, the filter unit 21 (glass sieve) and the infusion unit 2 are installed in the reaction tank 1. Through a PVC tube, the syringe is connected with an infusion pump (figures not shown), so as to infuse the solutions with a determined flow speed into the reaction tank 1, respectively. In this embodiment, the flow speeds are set as follow: bioactive agent containing-aqueous solution: 0.30 mL/h (relative mid-speed), organic solution: 0.15 mL/h (relative low-speed), aqueous solution: 0.50 mL/h (relative high-speed).

Step 102: Infusing the aqueous solution S1 and organic solution S2 into the reaction tank 1 of the device 1 and thus forming an interface between the filter 21 and the collector 11 (as shown in FIG. 2).

Step 103: Infusing the bioactive agent containing-aqueous solution S3 and being filtered by the filter 21, the bioactive agent droplet is surrounded by the organic solution S2 to form a water-in-oil emulsion (as shown in FIG. 1C).

Step 104: The water-in-oil emulsion is passing through the aqueous solution 51 and form a water-in-oil-in-water double emulsion (as shown in FIG. 1D).

Step 105: Removing the organic phase of water-in-oil-in-water double emulsion in step 104 so as to harvest a plurality of liposomes. For example, in this embodiment, a rotary evaporator is used to remove the chloroform to obtain the liposomes.

Step 106: The unencapsulated part of the bioactive agent containing-aqueous solution S3 in step 105 is removed. For example, dialysis method is used to remove fluorescence dye (5(6)-carboxyfluorescein) of the solution.

For the results can be easily detected, a glass sieve having pore size of 5-10 μm can used in foregoing steps to obtain larger size liposomes. Thus, after chloroform is removed, the results can be observed by fluorescence microscopes.

Figure 4:
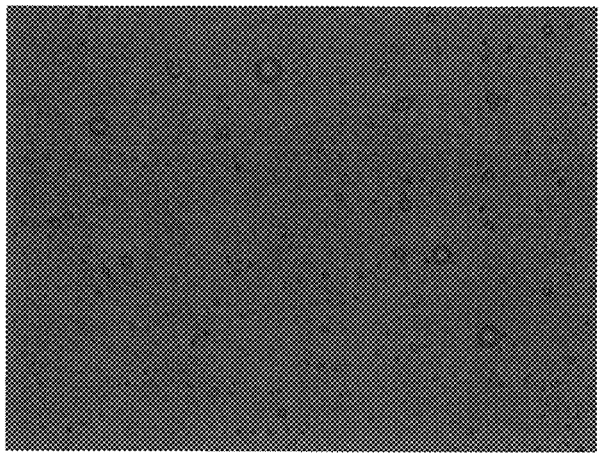
FIG. 4(A)-4(C) depict the fluorescence microscopy photos of (A) under phase contrast mode, (B) Nile red fluorescence, and (C) carboxyfluorescein fluorescence.
Figure 4:
Figure 4:
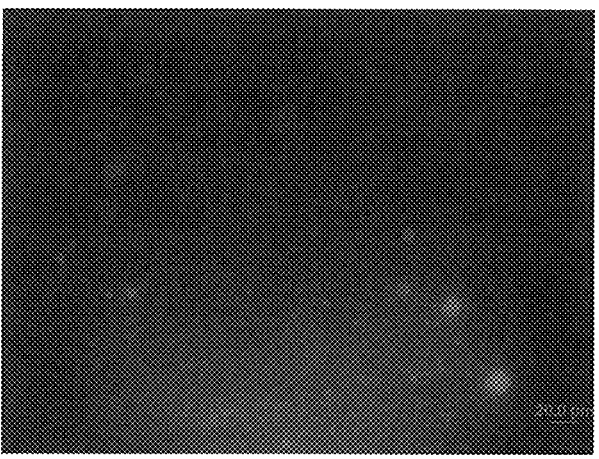

FIG. 4(A)-4(C) depict the fluorescence microscopy photos of (A) under phase contrast mode, (B) Nile red fluorescence, and (C) carboxyfluorescein fluorescence. As shown in photos, sphere particles are observed and their diameters are mostly less than 10 μm. As results shown in FIGS. 4(A)-4(C) that Nile red and carboxyfluorescein are simultaneously observed in the liposeomes.

To further detect the distribution of fluorescence dye in solution, a laser scanning confocal microscope can be used to observe the liposomes.

Figure 5:
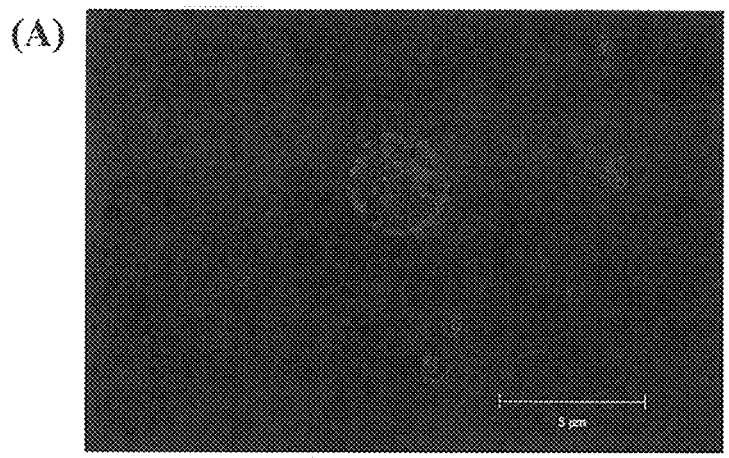
FIG. 5(A)-5(C) depict the fluorescence microscopy photos of (A) Nile red fluorescence, (C) carboxyfluorescein fluorescence, (C) overlapping image of (A) and (B)
Figure 5:
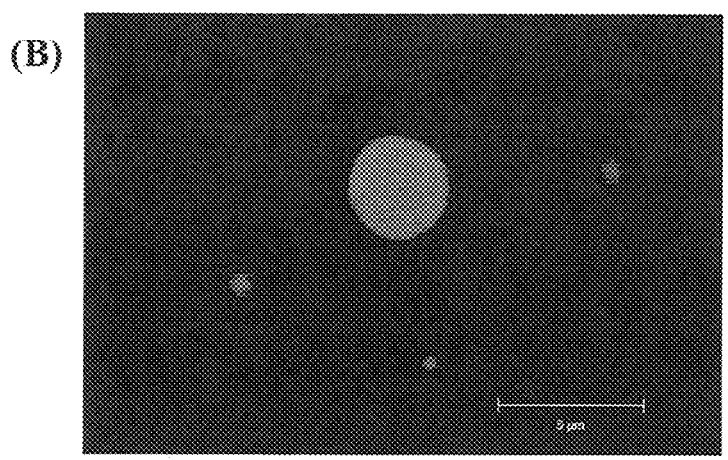
Figure 5:
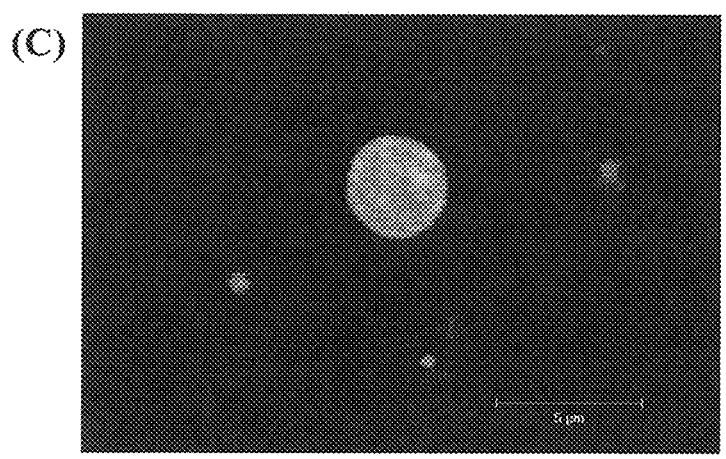
Figure 6:
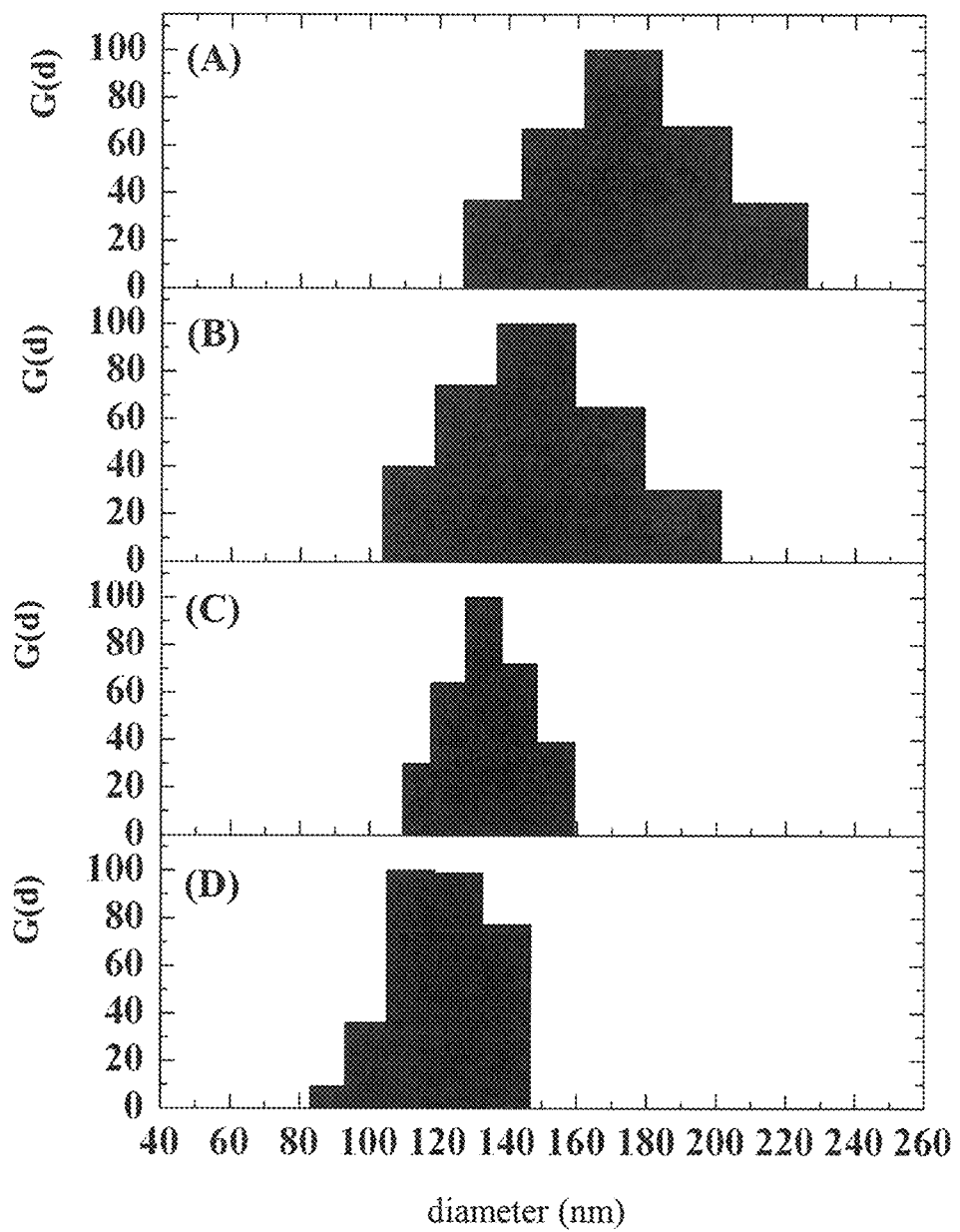
FIG. 6(A)-6(D) depict the particle size distribution of the double emulsion after natural evaporation, after (A) 14 hours, (B) 22 hours, (C) 36 hours, and (D) 46 hours.

FIG. 5(A)-5(C) depict the fluorescence microscopy photos of (A) Nile red fluorescence, (B) carboxyfluorescein fluorescence, (C) overlapping image of (A) and (B). As compared with FIGS. 5(A) and 5(B), hydrophobic fluorescence dye, Nile red, is distributed around the surface of spheres, and thus exhibits the distribution of phospholipid molecules of the spheres. On the other hand, hydrophilic fluorescence dye, carboxyfluorescein, is distributed inside the spheres. As shown in FIG. 5(C), an overlapped image of FIGS. 5(A) and 5(B), distribution of bioactive agents and phospholipids of a sphere is exhibited. To sum up, the spherical vehicles as manufactured in the present embodiment are the liposomes formed by the W/O/W double emulsion.

Embodiment 3

In contrast with large size liposomes produced in embodiment 2, a syringe filter having membrane pore size of 0.45 μm is used in this embodiment to produce smaller size liposomes. As using the syringe filter according to this embodiment, the flow speed of infusion pump is set to 0.20 mL/h. Except that, other steps are similar to embodiment 2, so the details are not repeated here.

The results are displayed in FIG. 6(A)-6(D). The figures depict the particle size distribution of the double emulsion after natural evaporation, separately after (A) 14 hours, (B) 22 hours, (C) 36 hours, and (D) 46 hours. In order to produce liposomes from the double emulsion in step 104, the double emulsion is placed for a while to evaporate the chloroform. A particle size analyzer is used to analyze the continuous change of the double emulsion size as chloroform evaporates. As shown in FIG. 6(A)-6(D), the size of the double emulsion according to this embodiment is decreased due to evaporation of chloroform (14, 22, 38 and 46 hours). After 46 hours, the size of the double emulsion is invariable and so as to form liposomes whose diameter is ¼ of the membrane pore size. To further shorten the preparation time, rotary evaporator is used to accelerate evaporation of chloroform. Under the condition as follow, 100 mbar, 50° C., evaporate for 30 min, liposomes are obtained with similar size as treated as nature evaporation for 46 hours.

Embodiment 4

The size of liposome produced by double emulsion method is determined by the size of water droplets (bioactive agent containing-aqueous solution). In this embodiment, two syringe filters having membrane pore size of 0.22 μm and 0.45 μm are used respectively, so as to examine liposome size influenced by different membrane pore size of filter, and thus analyzed by particle size analyzer.

Figure 7:
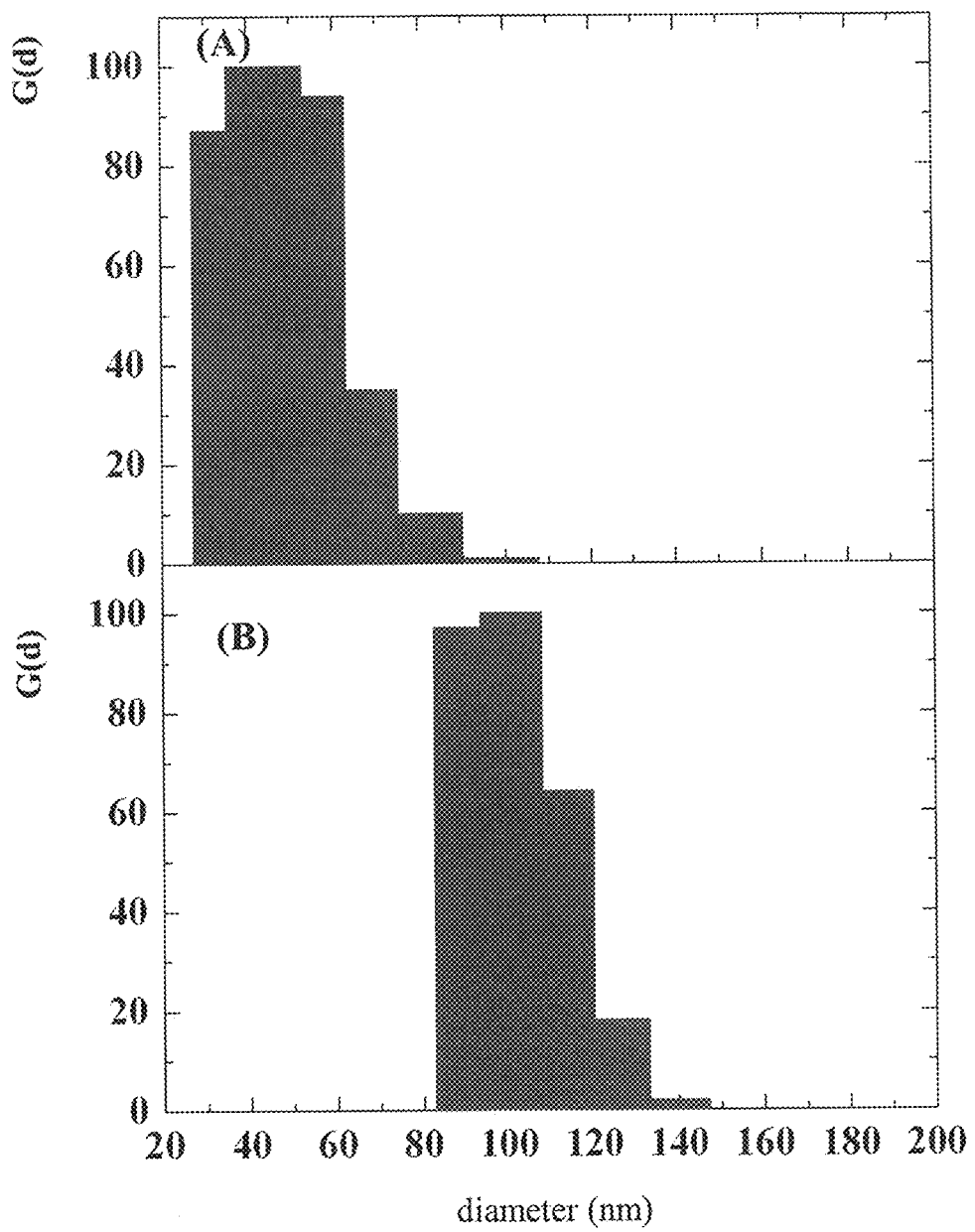
FIG. 7(A)-7(B) depict the particle size distribution of the liposomes prepared by syringe filter with membrane pore size of (A) 0.22 μm and (B) 0.45 μm.

As shown in FIG. 7(A)-7(B), the figures depict the particle size distribution of the liposomes prepared by syringe filter having membrane pore size of (A) 0.22 μm and (B) 0.45 μm. As analyzed by particle size analyzer, two liposome sizes are shown in FIG. 7(A)-7(B), respectively. The results identify that the liposome size generated by the device of the present invention is directly related with the membrane pore size of filter. And its diameter is approximately ¼ of the membrane pore size.

By a fluorescence spectrophotometer, the encapsulation efficiency of liposomes that encapsulate fluorescence dye can be obtained. The definition of encapsulation efficiency is defined as follow:

$$\frac{\text{amount of fluorescence dye encapsulated by liposome}}{\text{total amount of used fluorescence dye}} \times 100\% = \frac{\text{fluorescence dye obtained after liposomes disrupt}}{\text{fluorescence dye concentration of bioactive agent containing-aqueous solution}} \times 100\%$$

As calculated results, according to the calibration curve obtained from carboxyfluorescein standard (coefficient of determination, $R^2=0.994$), the encapsulation efficiency of carboxyfluorescein of liposomes generated by the device of the present invention is shown in table.1. The encapsulation efficiency percentages of the liposomes filtered by filters having membrane pore size of 0.22 μm and 0.45 μm are 24% and 28%, respectively.

TABLE 1

The encapsulation efficiency percentages of carboxyfluorescein of liposomes generated by the device of the present invention.

| encapsulation agent | membrane pore size | encapsulation efficiency |
|---|---|---|
| 5(6)-Carboxyfluorescein | 0.22 μm | 24% |
| | 0.45 μm | 28% |

The encapsulation efficiency of agents encapsulated by liposomes is significantly related with the method of producing liposomes. The composition of the liposomes may also be influential the encapsulation efficiency. As compared with the documents [1-5] and the method according to the present invention, the encapsulation efficiencies are exhibited in table.2. As shown in table.2, it is found that the encapsulation efficiencies of liposomes generated by thin-film hydration methods or reverse phase evaporation methods are commonly much lower than 30%. However, the encapsulation efficiency of liposomes according to the present invention is much higher. The encapsulation efficiency of liposomes generated by the device of the present invention is approximately 0.3, which is higher than the results in documents 1 and 3. It is proved that the device and method of the present invention can generate liposomes with high encapsulation efficiency.

TABLE 2

Documents of different liposome producing methods and the encapsulation efficiencies thereof.

| method | encapsulation agent | phospholipid composition | encapsulation efficiency |
|---|---|---|---|
| thin-film hydration method [1] | 5(6)-Carboxyfluorescein | DPPC/DPPG | 1.0% |
| | | POPC/POPG | 2.8% |
| thin-film hydration method [2] | DNA plasmid (plasmid DNA) | POPC/PLPC/SOPC | 27% |
| reverse phase evaporation method [3] | 5(6)-Carboxyfluorescein | Egg PC | 0.31-3.10% |
| reverse phase evaporation method [4] | Sodium mercaptoundeca-hydrododecarborate Hydrododecaborate | DSPC/DSPE-PEG | 6-8% |
| double emulsion method [5] | Calcein | Soybean PC | 62.6-69.2% |
| | | Soybean PC/PS | 73.5-78.4% |
| double emulsion method (present invention) | 5(6)-Carboxyfluorescein | DPPC/DPPG | ~26% |

Although the present invention has been described with reference to the preferred embodiments thereof, it is apparent to those skilled in the art that a variety of modifications and changes may be made without departing from the scope of the present invention which is intended to be defined by the appended claims.

REFERENCES

[1] Volodkin, D.; Mohwald, H.; Voegel, J. C.; Ball, V. *J. Control. Release* 2007, 117, 111-120.
[2] Sunami, T.; Sato, K.; Matsuura, T.; Tsukada, K.; Urabe, I.; Yomo, T. *Anal. Biochem.* 2006, 357, 128-136.
[3] de la Maza, A.; Parra, J. L. *Biophys. J.* 1997, 72, 1668-1675.
[4] Maruyama, K.; Ishida, O.; Kasaoka, S.; Takizawa, T.; Utoguchi, N.; Shinohara, A.; Chiba, M.; Kobayashi, H.; Eriguchi, M.; Yanagie, H. *J. Controlled Release* 2004, 98, 195-207.
[5] Wang, T.; Deng, Y.; Geng, Y.; Gao, Z.; Zou, J.; Wang, Z. *Biochim. Biophys. Acta-Biomembranes* 2006, 1758, 222-231.

What is claimed is:

1. A device for preparation of liposomes, which is programmable and adapted to manufacture liposomes, comprising:
    a reaction tank, comprising:
        a collector mounted in an upper portion of the reaction tank;
        a first inlet port set at the upper portion of the reaction tank for infusing an aqueous solution; and
        a second inlet port set at a lower portion of the reaction tank for infusing an organic solution;
    an infusion unit set at the lower portion of the reaction tank and being opposite to the collector, wherein the infusion unit has a first end in the reaction tank and a second end out of the reaction tank for introducing a bioactive agent containing-aqueous solution into the reaction tank; and
    a filter deposited at the first end in the reaction tank of the infusion unit and being adjacent to but separated from the collector.

2. The device as claimed in claim 1, wherein the filter is a syringe filter.

3. The device as claimed in claim 2, wherein the pore size of the syringe filter is preferably 0.03 μm or 1.0 μm.

4. The device as claimed in claim 1, wherein the filter is a glass sieve.

5. The device as claimed in claim 4, wherein the pore size of the glass sieve is preferably in a range of 1 μm~10 μm.

6. The device as claimed in claim 1, wherein the aqueous solution, the organic solution, and the bioactive agent containing-aqueous solution are infused into the reaction tank by an infusion pump with a determined fluid speed respectively.

7. A method for preparation of liposomes using the device as claimed in claim 1, comprising the steps of:
    (a) providing an aqueous solution, an organic solution, and a bioactive agent containing-aqueous solution;
    (b) infusing the aqueous solution and the organic solution into the reaction tank of the device and thus forming an interface between the filter and the collector;
    (c) infusing the bioactive agent containing-aqueous solution and being filtered by the filter, the bioactive agent of the solution is encapsulated to form a water-in-oil emulsion;
    (d) the water-in-oil emulsion is passing through the aqueous solution and thus to form a water-in-oil-in-water double emulsion; and
    (e) removing the organic phase of water-in-oil-in-water double emulsion so as to harvest a plurality of liposomes.

8. The method as claimed in claim 7, further comprising a step (f) after step (e): removing the bioactive agent containing-aqueous solution without being encapsulated.

9. The method as claimed in claim 7, wherein the step (e) further uses a rotary evaporator to facilitate the removal of the organic phase.

10. The device as claimed in claim 7, wherein the fluid speed ratio of the aqueous solution, the organic solution, and the bioactive agent containing-aqueous solution, is preferably 0.3:0.15:0.2~0.5.

11. The device as claimed in claim 7, wherein the organic solution is consisting of an organic solvent and at least a phospholipid.

12. The device as claimed in claim 11, wherein the phospholipid is selected from a group consisting of dipalmitoylphosphatidylcholine (DPPC) and dipalmitoylphosphatidyl glycerol (DPPG) and thereof.

13. The device as claimed in claim 11, wherein the organic solution is further containing a hydrophobic substance.

14. The device as claimed in claim 13, wherein the hydrophobic substance is a fluorescence dye, drug, or contrast agent.

15. The device as claimed in claim 7, wherein the bioactive agent containing-aqueous solution further contains a hydrophilic substance.

16. The device as claimed in claim 15, wherein the hydrophilic substance is a fluorescence dye, drug, protein, apamer or contrast agent.

* * * * *